(12) United States Patent
Groome et al.

(10) Patent No.: US 8,383,351 B2
(45) Date of Patent: Feb. 26, 2013

(54) ANTIBODY TO INHIBIN/ ACTIVIN β-B SUBUNIT

(75) Inventors: Nigel Patrick Groome, Chipping Norton (GB); Helen Ludlow, Woodins Way (GB)

(73) Assignee: Oxford Brookes University (GB)

( * ) Notice: Subject to any disclaimer, the term of this patent is extended or adjusted under 35 U.S.C. 154(b) by 578 days.

(21) Appl. No.: 12/482,961

(22) Filed: Jun. 11, 2009

(65) Prior Publication Data

US 2009/0317921 A1    Dec. 24, 2009

Related U.S. Application Data

(60) Provisional application No. 61/060,491, filed on Jun. 11, 2008.

(51) Int. Cl.
*G01N 33/53* (2006.01)
*C07K 16/00* (2006.01)
*C07K 16/28* (2006.01)

(52) U.S. Cl. ........... 435/7.1; 530/387.1; 530/388.24

(58) Field of Classification Search .............. None
See application file for complete search history.

(56) References Cited

U.S. PATENT DOCUMENTS

| | | | | |
|---|---|---|---|---|
| 5,859,205 A | * | 1/1999 | Adair et al. ............ | 530/387.3 |
| 7,842,472 B2 | * | 11/2010 | Valkirs et al. ............ | 435/7.21 |
| 2010/0285974 A1 | * | 11/2010 | Horne et al. ............ | 506/7 |

FOREIGN PATENT DOCUMENTS

WO    WO/2009/004340    * 1/2009

OTHER PUBLICATIONS

Wang et al. Preparation and identification of human inhibin beta-B subunit monoclonal antibody. Henan Yike Daxue Xuebao, 34(4):8-10, 1999. Abstract only.*
Sun et al. Synthesis of human inhibin beta B fragments, preparation and generation of monoclonal antibodies against human inhibin beta B subunits. Yaoxue Xuebao, 35(7):505-507, 2000. Abstract only.*
Klimka et al.,Human anti-CD30 recombinant antibodies by guided phage antibody selection using cell panning. British Journal of Cancer (2000) 83:252-260.*
Beiboer et al., Guided selection of a pan carcinoma specific antibody reveals similar binding characteristics yet structural divergence between the original murine antibody and its human equivalent. J. Mol. Biol. 296: 833-849 (2000).*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Eduardo Padlan, Anatomy of the antibody molecule. Mol Immunol. Feb. 1994;31(3):169-217.*
Portolano et al., Lack of promiscuity in autoantigen-specific H and L chain combinations as revealed by human H and L chain "roulette". J Immunol. Feb. 1, 1993;150(3):880-7.*
Ludlow et al. Development of a new antibody to the human inhibin/activin betaB subunit and its application to improved inhibin B ELISAs. J Immunol Methods. Jan. 1, 2008 ;329(1-2):102-11. Epub Oct. 23, 2007.*
Altschul et al., (1990) J. Mol. Biol. 215:403-410.
Altschul et al., (1977) Nuc. Acids Res. 25:3389-3402.
Andersen et al. (2004) J. Immunoassay Immunochem. 25:17.
Attardi et al. (1992) Endocrinol. 130:557.
Burger et al. (1988) J. Clin. Endocrinol. Metab. 66:885.
Burger et al. (1998) J. Clin. Endocrinol. Metab. 83:4167.
Caterson et al. (1983) J. Biol. Chem. 258:8848.
Cunningham et al., (1970) J. Biol. Chem., 9, 3161.
Fowers et al. (2001) J. Drug Target 9:281.
Groome et al. (1990) Hybridoma 9:31.
Groome et al. (1996) J. Clin. Endocrinol. Metab. 81:1401).
Henikoff & Henikoff, (1989) Proc. Natl. Acad. Sci. USA 89:10915.
Illingworth et al. (1996) J. Clin. Endocrinol. Metab. 81:1321.
Ismail et al. (2002) Clin. Chem. 48:2023.
Kishiro et al. (1995) Cell Struct. Funct. 20:151.
Knight et al. (2001) Reproduction 121:503.
Knight et al. (1994) J. Endocrinol. 141:417.
Knight et al. (1996) J. Endocrinol. 148:267.
Kohler et al., (1975) Nature 256:495.
Kricka et al., (1999) Clin. Chem. 45:942.
Lambert-Messerlian et al. (2007) Clin. Chem. 53:800.
Lamoyi et al., (1986) Methods Enzymol. 121:652.
Ling et al. (1986) Biochem. Biophys. Res. Commun. 138:1129.
Man et al., Epitope Mapping Protocols in Methods in Molecular Biology, vol. 66, G. E., Aug. 1, 1996.
Marks et al., (2002) Clin. Chem. 48:2008.
Mason et al., (1986) Biochem. Biophys. Res. Commun. 135:957.
Milenic et al., (1989) J. Immunol. Methods 120:71.
Mirza et al., (1987) J. Immunol. Methods 105:235.
Miyamoto et al., (1985) Biochem. Biophys. Res. Commun. 129:396.
Morgan et al., (2001) J. Urol. 166:2311.
Muttukrishna et al., (2000) Hum. Reprod. 15:549.
Pearson et al., (1997) Genomics 46:24.
Robertson et al., (1985) Biochem. Biophys. Res. Commun. 126:220.
Robertson et al., (2002) J. Clin. Endocrinol. Metab. 87:816.
Robertson et al., (2004) Endocr. Relat. Cancer 11:35.
Robertson et al., (2004) Mol. Cell Endocrinol. 225:65.
Sado et al., (2006) Acta Histochem. Cytochem. 39:89.
Vale et al., (1986) Nature 321:776.
Vale et al., (1988) Recent Prog. Horm. Res. 44:1.
Wald et al., (2003) Lancet 361:835.
Wallace et al., (1998) Ann. Clin. Biochem. 35:656).
Weber et al., (1990) Scand. J. Clin. Lab Invest. Supp. 201:77.
Wong et al., (1993) J. Immunol. Methods 165:1.
Woodruff et al., (1996) Endocrinology 137:5463.
Wring et al., (1999) J. Pharm. Biomed. Anal. 19:695.
Yamaguchi et al., (1995) J. Immunol. Methods 181:259.

* cited by examiner

*Primary Examiner* — Maher Haddad
(74) *Attorney, Agent, or Firm* — Merchant & Gould P.C.

(57) ABSTRACT

The present invention provides an improved antibody specific for the inhibin/activin beta-B subunit polypeptide. The antibody is highly specific for the beta-B subunit in a sample, and does not require processing of the sample with heat or oxidizing agents. Thus, discovery of the new antibody provides for simpler, more accurate immunoassays for a wider range of sample types.

8 Claims, 2 Drawing Sheets

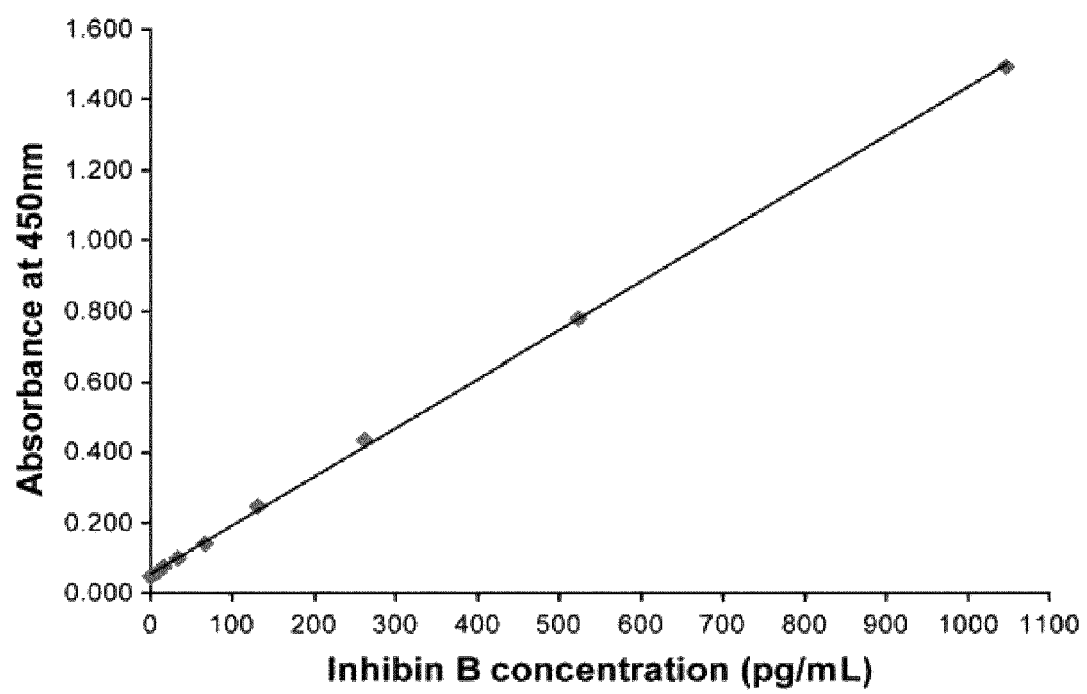
Fig. 1. Typical standard curve in the improved inhibin B assay.

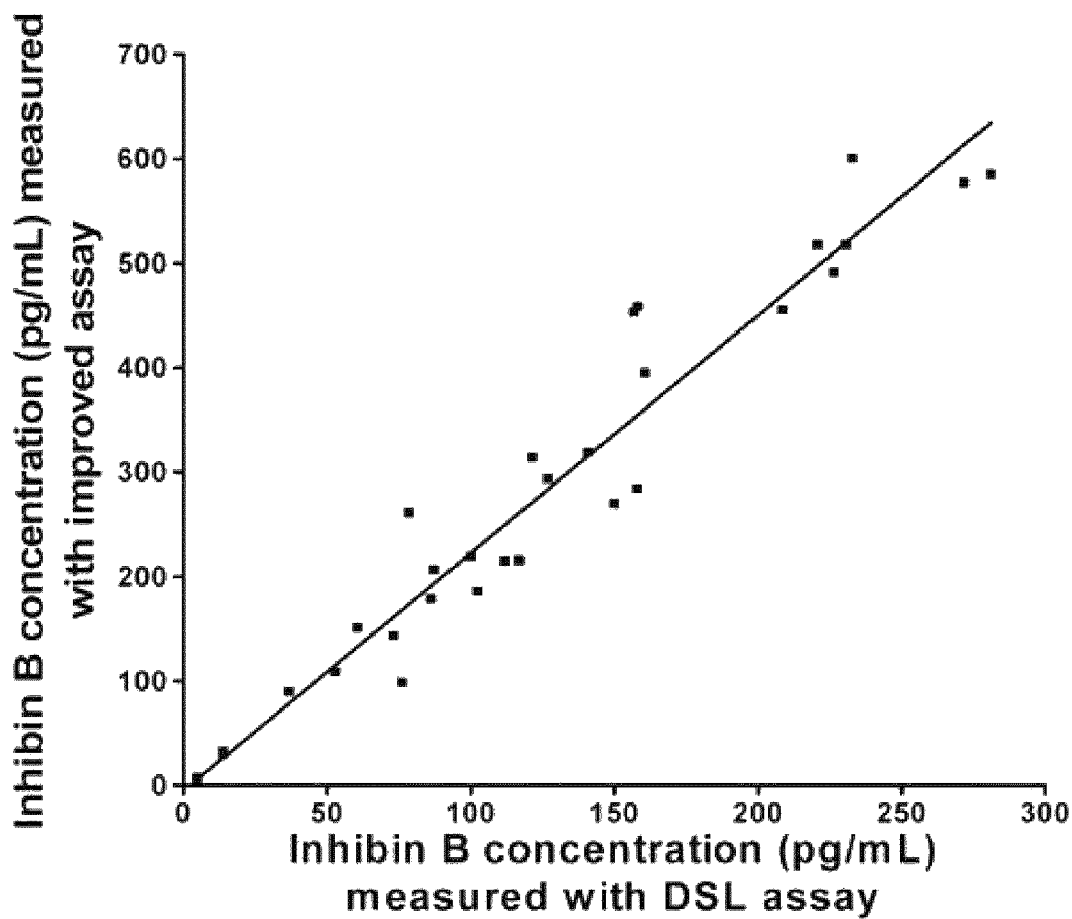
Fig. 2. Relationship between inhibin B concentrations (pg/ml) obtained with both the DSL and improved inhibin B assays for 58 human serum samples. Linear regression analysis results were as follows: r= 0.98; P b0.0001; y = 0.4101x+ 10.53

SEQUENCE LISTING

<160> NUMBER OF SEQ ID NOS: 2

<210> SEQ ID NO 1
<211> LENGTH: 165
<212> TYPE: PRT
<213> ORGANISM: Mus musculus

<400> SEQUENCE: 1

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Ser Tyr Phe His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Thr Met Glu Ala Glu Asp Ala Val Thr Tyr Tyr Cys His
            100                 105                 110

Gln Tyr His Arg Ser Pro Trp Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys
                165

<210> SEQ ID NO 2
<211> LENGTH: 157
<212> TYPE: PRT
<213> ORGANISM: Mus musculus

<400> SEQUENCE: 2

Met Lys Cys Ser Trp Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Met Tyr Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Gly Lys Phe Lys Thr Gly Ala Thr Leu Thr Val Asp Lys Ser Ser Ser
                85                  90                  95

Thr Val Tyr Met Gln Leu Ser Ser Leu Thr Ser Glu Asp Ser Ala Val
            100                 105                 110

Tyr Tyr Cys Ala Arg Trp Gly Tyr Gly Gly Asn Tyr Asp Tyr Ala Met
        115                 120                 125

```
-continued

Asp Tyr Trp Gly Gln Gly Thr Ser Val Thr Val Ser Ser Ala Lys Thr
    130             135             140

Thr Pro Pro Ser Val Tyr Pro Leu Ala Pro Gly Ser Leu
145             150             155
```

ANTIBODY TO INHIBIN/ACTIVIN β-B SUBUNIT

CROSS-REFERENCES TO RELATED APPLICATIONS

The present application claims benefit to U.S. Provisional Application No. 61/060,491, filed Jun. 11, 2008, which is incorporated by reference in its entirety.

BACKGROUND OF THE INVENTION

Inhibins are members of the transforming growth factor β (TGF-β) superfamily and are dimeric in structure (Evans and Groome (2001) Development of Immunoassays for Inhibin, Activin and Follistatin. In: S. Muttukrishna and W. Ledger (Eds.) Inhibin, Activin and Follistatin in Human Reproductive Physiology. [Imperial College Press, London], pp. 11-60; Robertson et al. (2004) *Endocr. Relat.* Cancer 11:35; Robertson et al. (2004) *Mol. Cell. Endocrinol.* 225:65). They regulate the reproductive system by acting on the pituitary gland and blocking the synthesis of the FSH-β subunit and therefore the secretion of FSH (Burger and Igarashi (1988) *J. Clin. Endocrinol. Metab.* 66:885; Attardi et al. (1992) *Endocrinol.* 130:557; Burger et al. (1998) *J. Clin. Endocrinol. Metab.* 83:4167; Knight and Glister (2001) *Reproduction* 121:503). Inhibins are heterodimeric molecules containing an β subunit and either a βA or βB subunit, which are connected to each other by a disulfide bond. If the dimer consists of a βA subunit the molecule is called inhibin A, and if it consists of a βB subunit the molecule is called inhibin B (Miyamoto et al. (1985) *Biochem. Biophys. Res. Commun.* 129:396; Robertson et al. (1985) *Biochem. Biophys. Res. Commun.* 126:220; Mason et al. (1986) *Biochem. Biophys. Res. Commun.* 135:957). Activins contain two β subunits and can be homodimeric or heterodimeric depending on the arrangement of their subunits (Ling et al. (1986) *Biochem. Biophys. Res. Commun.* 138:1129; Vale et al. (1986) *Nature* 321:776). Two βA subunits make activin A, two βB subunits make activin B and a βA subunit attached to a βB subunit make activin AB (Vale et al., 1986; Vale et al. (1988) *Recent Prog. Horm. Res.* 44:1).

The measurement of inhibins in biological fluids has led to insights into its physiology, such as the pattern of inhibins in the menstrual cycle (Groome et al. (1996) *J. Clin. Endocrinol. Metab.* 81:1401). Some of the many applications include; Down's syndrome screening (inhibin A), male infertility testing (inhibin B), ovarian reserve/menopause onset (inhibin B) and ovarian cancer (inhibin αC subunit and inhibin B) (Illingworth et al. (1996) *J. Clin. Endocrinol. Metab.* 81:1321; Muttukrishna et al. (2000) *Hum. Reprod.* 15:549; Robertson et al. (2002) *J. Clin. Endocrinol. Metab.* 87:816; Wald et al. (2003) *Lancet* 361:835).

Two commercial inhibin B immunoassays are available, from DSL and OBI. Both assays use the same pair of monoclonal antibodies raised to synthetic peptides generated over 10 years ago. The capture antibody (C5), was raised to a peptide from the βB subunit of inhibin, and the detection antibody (R1) was raised to a peptide from the α subunit of inhibin. Both assays require a methionine oxidation step with hydrogen peroxide to allow the C5 antibody to recognize its epitope, which contains the amino acid sequence MSM. The original use of an oxidation step was used by Knight and Muttukrishna (1994) *J. Endocrinol.* 141:417, who showed that it improved sensitivity of the inhibin A assay, and subsequently improved the activin A assay (Knight et al. (1996) *J. Endocrinol.* 148:267). Hydrogen peroxide is used to oxidize methionine to methionine sulfoxide in order for C5 to bind. The OBI assay also uses a SDS and heat pre-treatment (Wallace et al. (1998) *Ann. Clin. Biochem.* 35:656) of the sample to destroy any catalases that may affect the oxidation step (especially in haemolysed samples), destroy any proteases that may be present, remove binding proteins and remove potential false positive causing reagents (Evans and Groome, 2001). The OBI and DSL assays have a detection limit of approximately 7 pg/ml, and the cross-reactivity of the inhibin B assays with inhibin A was initially reported as approximately 0.5% (Groome et al., 1996). Adequate sensitivity of the present assays requires overnight incubation with the sample.

Several unsuccessful attempts to generate a superior replacement for the C5 antibody using synthetic peptide immunogens prompted the present alternative approach. The present invention is based on part on the discovery and development of antibodies to the βB subunit of inhibin/activin which are superior tools for immunoassay and immunohistochemistry.

BRIEF SUMMARY OF THE INVENTION

Methods and systems relating to immunoassays for the quantification of proteins are described herein. More specifically, the immunoassays described herein relate to the quantification of inhibin/activin beta-B subunit.

In some embodiments, the invention provides a composition comprising a monoclonal antibody binding to an inhibin beta-B subunit, wherein binding of said antibody does not require oxidation of said inhibin beta-B subunit or antibody-binding epitope thereof. In some embodiments, the antibody does not demonstrate significant binding to an inhibin beta-A subunit. In some embodiments, the antibody crossreacts with the inhibin/activin beta-A subunit less than 0.5%, e.g., less that 0.1, 0.05, 0.01, or 0.005%.

In some embodiments, said antibody comprises at least one complementarity determining region (CDR) from the light chain variable region sequence of SEQ ID NO:1. In some embodiments, said antibody comprises at least two CDRs from the light chain variable region sequence of SEQ ID NO:1. In some embodiments, said antibody comprises three CDRs from the light chain variable region sequence of SEQ ID NO:1. In some embodiments, the antibody comprises a light chain variable region with substantial identity to SEQ ID NO:1, e.g., 85, 90, 93, 95, 96, 97, 98, or 99% identity. In some embodiments, the antibody comprises the light chain variable region sequence of SEQ ID NO:1.

In some embodiments, said antibody comprises at least one complementarity determining region (CDR) from the heavy chain variable region sequence of SEQ ID NO:2. In some embodiments, said antibody comprises at least two CDRs from the heavy chain variable region sequence of SEQ ID NO:2. In some embodiments, said antibody comprises three CDRs from the heavy chain variable region sequence of SEQ ID NO:2. In some embodiments, the antibody comprises a heavy chain variable region with substantial identity to SEQ ID NO:2, e.g., 85, 90, 93, 95, 96, 97, 98, or 99% identity. In some embodiments, the antibody comprises the heavy chain variable region sequence of SEQ ID NO:2.

In some embodiments, the invention provides an immunoassay system comprising a capture antibody, wherein said capture antibody binds to an inhibin/activin beta-B subunit, and wherein binding of said antibody does not require oxidation of said inhibin/activin beta-B subunit or antibody-binding epitope thereof. In some embodiments, the antibody comprises at least one, two, or three CDRs from the light chain variable region sequence of SEQ ID NO:1. In some embodiments, the antibody comprises a light chain variable region with substantial identity to SEQ ID NO:1. In some embodiments, the antibody comprises at least one, two, or three CDRs from the heavy chain variable region sequence of SEQ ID NO:2. In some embodiments, the antibody comprises a heavy chain variable region with substantial identity to SEQ ID NO:2.

In some embodiments, the invention provides an immunoassay method for measuring an amount of inhibin B in a sample, said method comprising the steps of: (i) binding a capture antibody to an inhibin beta-B subunit in a sample, thereby creating a bound capture antibody, wherein binding of said antibody does not require oxidation of said inhibin beta-B subunit or antibody-binding epitope thereof; (ii) binding a detection antibody to an inhibin alpha subunit in the sample, thereby creating a bound detection antibody; and (iii) measuring the amount of inhibin B in the sample, based on the amount of the bound detection antibody. In some embodiments, the method comprises the same steps, but the antibody to inhibin beta-B subunit is the detection antibody, and the inhibin alpha subunit antibody is the capture antibody. In some embodiments, the capture antibody is bound to or coupled with a solid support. In some embodiments, the detection antibody is coupled with or bound to a label.

In some embodiments, the invention provides an immunoassay method for measuring an amount of activin B in a sample, said method comprising the steps of: (i) binding a capture antibody to an activin beta-B subunit in a sample, thereby creating a bound capture antibody, wherein binding of said antibody does not require oxidation of said activin beta-B subunit or antibody-binding epitope thereof; (ii) binding a detection antibody to an activin beta-B subunit in the sample, thereby creating a bound detection antibody, wherein binding of said antibody does not require oxidation of said activin beta-B subunit or antibody-binding epitope thereof; and (iii) measuring the amount of activin B in the sample, based on the amount of the bound detection antibody. In some embodiments, the capture antibody is bound to or coupled with a solid support. In some embodiments, the detection antibody is coupled with or bound to a label.

In some embodiments, the invention provides an immunoassay method for measuring an amount of activin AB in a sample, said method comprising the steps of: (i) binding a capture antibody to an activin beta-B subunit in a sample, thereby creating a bound capture antibody, wherein binding of said antibody does not require oxidation of said activin beta-B subunit or antibody-binding epitope thereof; (ii) binding a detection antibody to an activin beta-A subunit in the sample, thereby creating a bound detection antibody; and (iii) measuring the amount of activin AB in the sample, based on the amount of the bound detection antibody. In some embodiments, the method comprises the same steps, but the antibody to activin beta-B subunit is the detection antibody, and the activin beta-A subunit antibody is the capture antibody. In some embodiments, the capture antibody is bound to or coupled with a solid support. In some embodiments, the detection antibody is coupled with or bound to a label.

In some embodiments, the invention provides an immunoassay kit for measuring an amount of inhibin B in a sample, comprising: (i) a capture antibody to an inhibin beta-B subunit, wherein binding of said antibody does not require oxidation of said inhibin beta-B subunit or antibody-binding epitope thereof; (ii) a detection antibody, wherein the detection antibody binds to an inhibin alpha subunit; (iii) a solid support capable of being coupled with the capture antibody; and (iv) a label capable of being coupled with the detection antibody. In some embodiments, immunoassay kit is the same except the antibody to inhibin beta-B subunit is used as the detection antibody, and the antibody to the inhibin alpha subunit is used as the capture antibody. In some embodiments, the capture antibody and detection antibody are from different species (e.g., a rabbit and a sheep, a mouse and a goat, etc.), or are conjugated to different labels/binding moieties (e.g., biotin and His-tag). In some embodiments, the solid support is coupled with or bound to the capture antibody. In some embodiments, the label is coupled with or bound to the detection antibody.

In some embodiments, the invention provides an immunoassay kit for measuring an amount of activin B in a sample, comprising: (i) a capture antibody to an activin B subunit, wherein binding of said antibody does not require oxidation of said activin beta-B subunit or antibody-binding epitope thereof; (ii) a detection antibody, wherein the detection antibody binds to an activin beta-B subunit, wherein binding of said antibody does not require oxidation of said activin beta-B subunit or antibody-binding epitope thereof; (iii) a solid support capable of being coupled with the capture antibody; and (iv) a label capable of being coupled with the detection antibody. In some embodiments, the capture antibody and detection antibody are from different species (e.g., a rabbit and a sheep, a mouse and a goat, etc.), or are conjugated to different labels/binding moieties (e.g., biotin and His-tag). In some embodiments, the solid support is coupled with or bound to the capture antibody. In some embodiments, the label is coupled with or bound to the detection antibody.

In some embodiments, the invention provides an immunoassay kit for measuring an amount of activin AB in a sample, comprising: (i) a capture antibody to an activin B subunit, wherein binding of said antibody does not require oxidation of said activin beta-B subunit or antibody-binding epitope thereof; (ii) a detection antibody, wherein the detection antibody binds to an activin beta-B subunit; (iii) a solid support capable of being coupled with the capture antibody; and (iv) a label capable of being coupled with the detection antibody. In some embodiments, immunoassay kit is the same except the antibody to activin beta-B subunit is used as the detection antibody, and the antibody to the activin beta-A subunit is used as the capture antibody. In some embodiments, the capture antibody and detection antibody are from different species (e.g., a rabbit and a sheep, a mouse and a goat, etc.), or are conjugated to different labels/binding moieties (e.g., biotin and His-tag). In some embodiments, the solid support is coupled with or bound to the capture antibody. In some embodiments, the label is coupled with or bound to the detection antibody.

Various embodiments of methods and systems described herein provide the ability to quantify the inhibin/activin beta-B subunit, inhibin B, activin B, and activin AB in a sample, and will expedite investigations of the physiological relevance of these molecules in a number of applications.

BRIEF DESCRIPTION OF THE DRAWINGS

The drawings form a part of the specification and are provided to aid in understanding of some aspects of the invention. It is to be noted, however, that the appended drawings illustrate exemplary embodiments of the invention and therefore are not to be considered limiting in their scope.

FIG. 1 is a typical standard curve in the improved inhibin B assay.

FIG. 2 shows the relationship between inhibin B concentrations (pg/ml) obtained with both the DSL and improved inhibin B assays for 58 human serum samples. Linear regression analysis results were as follows: r=0.98; P<0.0001; y=0.4101x+10.53.

DETAILED DESCRIPTION OF THE INVENTION

I. Definitions

Abbreviations include: DSL, Diagnostic Systems laboratories; ELISA, enzyme-linked immunosorbent assay; FCS, fetal calf serum; FSH, follicle stimulating hormone; HBR, heterophilic blocking reagent; HPLC, high-performance liquid chromatography; HRP, horseradish peroxidase; NIBSC, National Institute for Biological Standards and Control; OBI, Oxford Bio-Innovation: PEG, polyethylene glycol; PMS, post menopausal serum; PBS, phosphate buffered saline; RIMMS, repetitive immunisations multiple sites; SDS, sodium dodecyl sulfate; SDS-PAGE, sodium dodecyl sulfate-polyacrylamide gel electrophoresis; TMB, tetramethylbenzidine.

The terms "activin beta-B subunit," "inhibin beta-B subunit," "inhibin B beta subunit," and "inhibin/activin beta-B subunit" refer to the same subunit polypeptide. Similarly, the terms "activin beta-A subunit," "inhibin beta-A subunit," "inhibin A beta subunit," and "inhibin/activin beta-A subunit" refer to the same subunit polypeptide.

As used herein, an "inhibin" is a heterodimeric molecule containing an α subunit and either a βA or βB subunit, which are connected to each other by a disulfide bond. If the dimer consists of a βA subunit the molecule is called inhibin A, and if it consists of a βB subunit the molecule is called inhibin B. The inhibin can be from a human or non-human animal (e.g., horse, bovine, goat, dog, cat, sheep, rabbit, mouse, rat, non-human primate, manatee etc.), and inter-species sequence conservation is relatively high. An exemplary human alpha subunit sequence is disclosed as SwissProt Accession No. P05111.1. Exemplary human beta-A and beta-B subunit sequences are disclosed as SwissProt Accession Nos. P08476.2 and P09529.2, respectively.

An "activin" contains two β subunits and can be homodimeric or heterodimeric depending on the arrangement of their subunits. Two βA subunits make activin A, two βB subunits make activin B and a βA subunit attached to a βB subunit make activin AB. The activin can be from a human or non-human animal, e.g., horse, bovine, goat, dog, cat, sheep, rabbit, mouse, rat, non-human primate, etc.

Activins and inhibins can play opposing roles in diverse systems, including hypothalamic and pituitary hormone secretion, gonadal hormone secretion, germ cell development and maturation, erythroid differentiation, insulin secretion, nerve cell survival, embryonic axial development, and bone growth, depending on subunit composition.

Proteolytic processing yields a number of bioactive forms of the alpha and beta subunits. Both are initially expressed as proproteins, which are processed to produce the mature subunit forms. Each type can also be mono- or diglycosylated.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to VH-CH1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The term "domain" refers to a globular region of a heavy or light chain polypeptide comprising peptide loops (e.g., comprising 3 to 4 peptide loops) stabilized, for example, by pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). A heavy chain constant region is also commonly understood to refer collectively to the domains present in a full length constant region, which are CH1, hinge, CH2, and CH3 domains in the case of antibodies of IgG isotype. "Variable" domains on the light chain are referred to interchangeably as "light chain variable regions", "light chain variable domains", "VL" regions or "VL" domains). "Variable" domains on the heavy chain are referred to interchangeably as "heavy chain constant regions," "heavy chain constant domains," "CH" regions or "CH" domains).

The term "region" refers to a part or portion of an antibody chain and includes constant or variable domains as defined herein, as well as more discrete parts or portions of said domains. For example, variable domains or regions include "complementarity determining regions" or "CDRs" interspersed among "framework regions" or "FRs".

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

Those of skill in the art are familiar with characterization and relative positioning of antibody domains, CDRs and FRs. Antibody amino acids can be numbered by alignment with the human antibody EU (see Cunningham et al., *J. Biol. Chem.*, 9, 3161 (1970)). That is, the heavy and light chains of an antibody are aligned with the heavy and light chains of EU to maximize amino acid sequence identity and each amino acid in the antibody is assigned the same number as the corresponding amino acid in EU. The EU numbering system is conventional (see generally, Kabat et al. (1991) *Sequences of Protein of Immunological Interest*, NIH Publication No. 91-3242, US Department of Health and Human Services). The term "Kabat numbering" unless otherwise stated, is defined as the numbering of the residues as in Kabat et al.

As a general guide, the light chain CDRs fall approximately at the following amino acid positions: VL-CDR1: 24-34; VL-CDR2: 50-56; VL-CDR3: 89-97. The heavy chain CDRs fall approximately at the following amino acid positions: VH-CDR1: 31-35; VH-CDR2: 50-65; and VH-CDR3: 95-102. These ranges can vary, e.g., depending on the species from which the antibody is derived.

The following is a general guide for antibody residue alignment, and location of the CDRs in a light chain variable region. VL-CDR1 generally starts around residue 24, with a preceding Cys residue and a Trp residue following (e.g., Trp-Tyr-Gln, Trp-Leu-Gln, Trp-Phe-Gln, Trp-Tyr-Leu). VL-CDR1 is usually 10-17 residues. VL-CDR2 begins 16 residues after the end of VL-CDR1, and is generally preceded by Ile-Tyr, Val-Tyr, Ile-Lys, or Ile-Phe. VL-CDR2 is usually 7 residues in length. VL-CDR3 begins 33 residues after the end of VL-CDR2, and is generally preceded by a Cys residue. VL-CDR3 is usually 7-11 residues in length, and followed by Phe-Gly-Xxx-Gly.

The following is a general guide for locating the heavy chain variable region CDRs. VH-CDR1 usually starts at residue 26, four residues after a Cys. It is usually 10-12 residues in length, followed by a Trp (e.g., Trp-Val, Trp-Ile, Trp-Ala). VH-CDR2 starts 15 residues after the end of VH-CDR1, and is usually 16-19 residues in length. The preceding residues vary, but are commonly Leu-Glu-Trp-Ile-Gly. There are also variations in the following residues, which can be Lys, Arg-Leu, Ile, Val, Phe, Thr, Ala-Thr, Ser, or Ala. VH-CDR3 starts 33 residues after VH-CDR2, two residues after a Cys (e.g., Cys-Ala-Arg). The length can vary from 3-25 residues, but is generally followed by Trp-Gly-Xxx-Gly residues.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/; Altschul et al., *Nuc. Acids Res.* 25:3389-3402 (1977) and Altschul et al., *J. Mol. Biol.* 215:403-410 (1990)). Such sequences are then said to be "substantially identical." This definition also refers to, or can be applied to, the compliment of a test sequence. The definition also includes sequences that have deletions and/or additions, as well as those that have substitutions, as well as naturally occurring, e.g., polymorphic or allelic variants, and man-made variants. The algorithms can account for gaps and the like. Identity generally exists over a region that is at least about 25 amino acids or nucleotides in length, or over a region that is 50-100 amino acids or nucleotides in length.

The BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Modulators" of activity are used to refer to antagonists, inhibitors, activators, and agonists, e:g., identified using in vitro and in vivo assays for activity, e.g., inhibin or activin activity. Modulators can be naturally occurring, a mimetic based on a naturally occurring ligand, or synthetic. Assays to identify, e.g., a antagonist or agonist include, e.g., applying putative modulator compounds to a biological fluid, assay, or cell culture, in the presence or absence of an inhibin/activin beta-B subunit and then determining the functional effects on an activin or inhibin activity. Samples or assays comprising the beta-B subunit that are treated with potential modulators are compared to control samples without the modulators to examine the extent of effect. Control samples (untreated with modulators) are assigned a relative activity value of 100%. Inhibition is achieved when the inhibin/activin beta-B subunit activity relative to the control is significantly reduced (e.g., with reference to a desired statistical measure), as can be determined by one of skill in the art. Generally, activity of about 80%, 70%, 60%, 50%, or 25-1% of the control activity indicates the presence of an inhibitor. Activation is achieved when the activity relative to the control is significantly increased (e.g., with reference to a desired statistical measure), as can be determined by one of skill in the art. Generally, activity of about 110%, 125%, 150%, 200%, 300%, 500%, or 1000% or more of the control activity indicates the presence of an agonist.

Inhibin/activin beta-B subunit activities include dimerization, e.g., to the alpha subunit, or either A or B beta subunit. Inhibin and activin can act in the pituitary to inhibit or stimulate release of Folicular Stimulating Hormone (FSH), respectively.

The terms "reduce" and "increase" and similar relative terms are used herein to refer to a reductions, increases, etc. relative to a control value. Those of skill in the art are capable of determining an appropriate control for each situation. For example, if an agent is said to "reduce binding" of X to Y, the level of X-Y binding in the presence of the agent is reduced compared to the level of X-Y binding in the absence of the agent.

The term "compete for binding" refers to an interaction where more than one compound binds to a binding target in such a way that if a first compound is bound to the target, another compound cannot bind, or binds at a reduced level. In the context of the present invention, an agent is said to compete with the presently disclosed antibodies for binding to the inhibin/activin beta-B subunit polypeptide if the agent binds to substantially the same epitope or interferes with antibody binding to said epitope.

When referring to expression or activity, terms are generally not used in an absolute sense, as will be understood by one in the art. For example, if an agent "does not inhibit" or "does not bind to" a given polypeptide, it generally means that the agent does not have a statistically significant effect on the polypeptide, e.g., as compared to a control or range of controls. For example, when referring to an antibody, the term "requires oxidation of the epitope for binding," indicates that the antibody will not bind to the epitope with optimal affinity or avidity unless the epitope is oxidized. One of skill will understand, however, that there is almost always some low level of background contact between molecules in solution, that will likely occur even with a non-oxidized epitope.

II. Compositions of the Invention

The present invention discloses a composition comprising a monoclonal antibody, wherein said antibody binds to an epitope of an inhibin/activin beta-B subunit without prior oxidation of said epitope. In some embodiments, said antibody cross-reacts with an inhibin beta-A subunit less than 0.5%. In additional embodiments, the monoclonal antibody comprises an antibody or epitope-binding fragment that binds to the inhibin/activin beta-B subunit without prior oxidation of the subunit or antibody-binding epitope thereof. In some embodiments, the antibody comprises at least one CDR from the light chain variable region sequence of SEQ ID NO:1, e.g., one, two, or all three CDRs. In some embodiments, the antibody comprises a light chain variable region with substantial similarity to SEQ ID NO:1, e.g., 90, 92, 94, 95, 96, 97, 98, 99, or 100% sequence identity. In some embodiments, the antibody comprises at least one CDR from the heavy chain variable region sequence of SEQ ID NO:2, e.g., one, two, or all three CDRs. In some embodiments, the antibody comprises a heavy chain variable region with substantial similarity to SEQ ID NO:2, e.g., 90, 92, 94, 95, 96, 97, 98, 99, or 100% sequence identity.

Additional embodiments disclose an immunoassay system comprising an inhibin/activin beta-B subunit specific antibody, wherein said antibody binds to an epitope of an activin/inhibin beta-B subunit polypeptide without prior oxidation of said polypeptide of antibody-binding epitope thereof. In some embodiments, the antibody is used as a capture antibody, while in others, it can be used as a detection antibody. In some embodiments, the immunoassay system further comprises a different antibody, e.g., to the inhibin alpha subunit or the inhibin/activin beta-A subunit. Any of these antibodies can be used in combination as either the detection or capture antibody, as will be appreciated by one of skill.

In some embodiments, the invention provides an immunoassay kit for measuring an amount of an inhibin B in a sample, comprising a capture antibody, wherein the capture antibody binds to an epitope of an inhibin beta-B subunit polypeptide without prior oxidation of said polypeptide of antibody-binding epitope thereof; a detection antibody, wherein the detection antibody binds to an inhibin alpha subunit; a solid support coupled with the capture antibody;

and a label coupled with the detection antibody. The inhibin B kit can also be designed such that the inhibin alpha subunit antibody is the capture antibody and the inhibin beta-B antibody is the detection antibody.

In some embodiments, the invention provides an immunoassay kit for measuring an amount of activin B in a sample, comprising a capture and a detection antibody, wherein both antibodies bind to an epitope of an inhibin/activin beta-B subunit polypeptide without prior oxidation of said polypeptide of antibody-binding epitope thereof; wherein the detection antibody is or can be coupled with a label or detectable moiety and wherein the capture antibody is or can be coupled with a solid support. In some embodiments, the capture antibody and the detection antibody are from different species, or are linked to different tags, so that they can be distinguished.

In some embodiments, the invention provides an immunoassay kit for measuring an amount of an activin AB in a sample, comprising a capture antibody, wherein the capture antibody binds to an epitope of an inhibin/activin beta-B subunit polypeptide without prior oxidation of said polypeptide of antibody-binding epitope thereof; a detection antibody, wherein the detection antibody binds to an activin beta-A subunit; a solid support coupled with the capture antibody; and a label coupled with the detection antibody. The activin AB kit can also be designed such that the activin beta-A subunit antibody is the capture antibody and the activin beta-B antibody is the detection antibody.

III. Methods of the Invention

An embodiment of a method of the invention is an immunoassay method for measuring an amount of inhibin B in a sample, comprising the steps of binding a capture antibody to an epitope of an inhibin beta-B subunit polypeptide in a sample, thereby creating a bound capture antibody; binding a detection antibody to an inhibin alpha subunit polypeptide in the sample, thereby creating a bound detection antibody; and measuring an amount of the inhibin B in the sample based on the amount of the bound detection antibody, wherein the capture antibody binds to the epitope of the inhibin beta-B subunit polypeptide without prior oxidation of the polypeptide or antibody-binding epitope thereof. In some embodiments, the sample comprises a biological fluid. The method can, of course, be adjusted such that the alpha subunit antibody is used as the capture antibody, and the beta-B subunit antibody is used as the detection antibody.

The invention also provides methods for measuring an amount of activin B in a sample, comprising the steps of binding a capture antibody to an epitope of the inhibin/activin beta-B subunit polypeptide in a sample, thereby creating a bound capture antibody; binding a detection antibody to an inhibin/activin beta-B subunit polypeptide in the sample, thereby creating a bound detection antibody; and measuring an amount of the activin B in the sample based on the amount of the bound detection antibody, wherein the capture and detection antibodies bind to the epitope of the inhibin beta-B subunit polypeptide without prior oxidation of the polypeptide or antibody-binding epitope thereof. In some embodiments, the sample comprises a biological fluid.

The invention also provides methods for measuring an amount of activin AB in a sample, comprising the steps of binding a capture antibody to an epitope of an inhibin/activin beta-B subunit polypeptide in a sample, thereby creating a bound capture antibody; binding a detection antibody to an inhibin/activin beta-A subunit polypeptide in the sample, thereby creating a bound detection antibody; and measuring an amount of activin AB in the sample based on the amount of the bound detection antibody, wherein the capture antibody binds to the epitope of the inhibin beta-B subunit polypeptide without prior oxidation of the polypeptide or antibody-binding epitope thereof. In some embodiments, the sample comprises a biological fluid. The method can, of course, be adjusted such that the activin beta-A subunit antibody is used as the capture antibody, and the activin beta-B subunit antibody is used as the detection antibody.

The immunoassay can be immunometric, "two-site" or "sandwich" immunoassay, wherein the analyte is bound to or sandwiched between two antibodies that bind to different epitopes on the analyte. Representative examples of such immunoassays include enzyme immunoassays or enzyme-linked immunosorbent assays (EIA or ELISA), immunoradiometric assays (IRMA), fluorescent immunoassays, lateral flow assays, diffusion immunoassays, immunoprecipitation assays, and magnetic separation assays (MSA). As an example, a first antibody, which is described as the "capture" antibody, is bound to a solid support, such as a protein coupling or protein binding surface, colloidal metal particles, iron oxide particles, or polymeric beads (e.g., latex particles). The capture antibody can be bound to or coated on a solid support as known in the art. Alternatively, the capture antibody is coupled with a ligand that is recognized by an additional antibody that is bound to or coated on a solid support. Binding of the capture antibody to the additional antibody via the ligand then indirectly immobilizes the capture antibody on the solid support.

The second antibody, which is described as the "detection" antibody, is coupled or conjugated with a label using procedures known in the art. Examples of suitable labels for this purpose include a chemiluminescent agent, a colorimetric agent, an energy transfer agent, an enzyme, a substrate of an enzymatic reaction, a fluorescent agent and a radioisotope. In some embodiments, the label includes a first protein such as biotin coupled with the second antibody, and a second protein such as streptavidin that is coupled with an enzyme. The second protein binds to the first protein. The enzyme produces a detectable signal when provided with substrate(s), so that the amount of signal measured corresponds to the amount of second antibody that is bound to the analyte. Examples of enzymes include, without limitation, alkaline phosphatase, amylase, luciferase, catalase, beta-galactosidase, glucose oxidase, glucose-6-phosphate dehydrogenase, hexokinase, horseradish peroxidase, lactamase, urease and malate dehydrogenase. Suitable substrates include, without limitation, TMB (3,3',5,5'-tetramethyl benzidine, OPD (o-phenylene diamine), and ABTS (2,2'-azino-bis(3-ethylbenzthiazoline-6-sulfonic acid).

IV. Components of the Systems and Methods of the Invention

A. Target Proteins and Samples

In some embodiments, a sample in which an inhibin/activin beta-B or activin beta-B protein is measured is a biological fluid in which the protein naturally occurs. Examples include, blood, serum, plasma, urine, tears, saliva, lymph, cerebrospinal fluid, mucous, etc. Examples of human serum samples include non-pregnant serum, pregnancy serum from the first, second or third trimester. Still another suitable biological sample is amniotic fluid. Other samples may include cell cultures and non-naturally occurring or synthetic solutions containing inhibin B or activin B proteins.

B. Antibodies

Antibodies useful in the various embodiments of the systems and methods described herein include commercially available antibodies and antibody fragments, as well as any novel antibodies generated to bind a suitable epitope on the designated target protein. The antibodies used in various embodiments exemplified herein can be monoclonal or polyclonal in nature. Other antibodies and antibody fragments, such as recombinant antibodies, chimeric antibodies, humanized antibodies, antibody fragments such as Fab or Fv fragments, as well as fragments selected by screening phage display libraries, and the like are also useful in the compositions and methods described herein.

Methods for preparation of monoclonal as well as polyclonal antibodies are well established (Harlow E. et al., 1988. Antibodies. N.Y.: Cold Spring Harbour Laboratory). Polyclonal antibodies are raised in various species including but not limited to mouse, rat, rabbit, goat, sheep, donkey and horse, using standard immunization and bleeding procedures. Animal bleeds with high titres are fractionated by routine selective salt-out procedures, such as precipitation with ammonium sulfate and specific immunoglobulin fractions being separated by successive affinity chromatography on Protein-A-Sepharose and leptin-Sepharose columns, according to standard methods. The purified polyclonal as well as monoclonal antibodies are then characterized for specificity and lack of cross-reactivity with related molecules. Such characterization is performed by standard methods using proteins, for example inhibin B and activin B, labeled with a tracer such as a radioisotope or biotin in competition with increasing levels of unlabeled potential cross-reactants for antibody binding. In some embodiments, further purification is required to obtain highly specific antibody fractions or for selection of higher affinity antibody fractions from a polyclonal pool. In the case of monoclonal antibodies, care is taken to select antibodies with good binding characteristics and specificity not only for the immunogen, but also for the native circulating molecules, particularly when a recombinant molecule or peptide antigen is used for immunization.

Cross-reactivity studies are further evaluated by other standard methods such as the well-established sodium dodecyl sulphate-polyacrylamide gel electrophoresis (SDS-PAGE) and Western immunoblot methods under reducing and non-reducing conditions. Evaluation of protein immunoreactivity detected in serum samples fractionated by high performance liquid chromatography (HPLC) is also used to roughly define the molecular weight profile of the protein detected.

Monoclonal antibodies can be prepared according to well established standard laboratory procedures ("Practice and Theory of Enzyme Immunoassays" by P. Tijssen (In Laboratory Techniques in Biochemistry and Molecular Biology, Eds: R. H. Burdon and P. H. van Kinppenberg; Elsevier Publishers Biomedical Division, 1985)), which are based on the original technique of Kohler and Milstein (Nature 256:495, 1975). This technique is performed by removing spleen cells from immunized animals and immortalizing the antibody producing cells by fusion with myeloma cells or by Epstein-Barr virus transformation, and then screening for clones expressing the desired antibody, although other techniques known in the art are also used. Antibodies are also produced by other approaches known to those skilled in the art, including but not limited to immunization with specific DNA.

As known in the art, a capture antibody can be coupled with or linked to various solid phase supports using standard non-covalent or covalent binding methods, depending on the required analytical and/or solid-phase separation requirements. The solid-support can be in the form of test tubes, beads, microparticles, filter paper, membranes, glass filters, magnetic particles, glass or silicon chips or other materials and approaches known to those skilled in the art. The use of microparticles, particularly magnetizable particles, that have been directly coated with the antibody (magnetic particles-capture antibody) or particles that have been labeled with a universal binder (e.g., avidin or anti-species antibody) is useful for significantly shortening the assay incubation time. These along with other alternative approaches known in the art allow for assay completion within minutes without limiting the required sensitivity. The use of magnetizable particles or similar approaches allow for convenient automation of the technology on the widely available immunoanalyzers.

The detection antibody used for detection of a given polypeptide antigen can be coupled with a detectable moiety. The detection antibody can then be detected either directly with a reporter molecule, or detected indirectly by a secondary detection system. The latter is based on several different principles known in the art, including antibody recognition by a labeled anti-species antibody and other forms of immunological or non-immunological bridging and signal amplification detection systems (e.g., the biotin-streptavidin technology). The signal amplification approach is used to significantly increase the assay sensitivity and low level reproducibility and performance. The label used for direct or indirect antibody coupling is any detectable reporter molecule. Examples of suitable labels are those widely used in the field of immunological and non-immunological detection systems, such as fluorophores, luminescent labels, metal complexes and radioactive labels, as well as moieties that could be detected by other suitable reagents such as enzymes, or various combinations of direct or indirect labels such as enzymes with luminogenic substrates.

V. Applications of the Present Invention

The presently described antibodies and immunoassay systems can be used in all of the same applications as the prior art antibodies, and more, as the present antibodies do not require harsh pretreatment of samples in order to bind. The present invention can therefore be used to detect or monitor a wide range of physiological conditions, including variations in the menstrual cycle, granulosa cell tumors, Down's syndrome, male infertility (e.g. sertoli cell function), ovarian reserve/menopause onset, and ovarian cancer.

Although specific embodiments of the invention, including the following examples, are described for purposes of illustration, various modifications can be made without deviating from the spirit and scope of the invention. Accordingly, the invention is not limited to the specific embodiments disclosed. All publications, patents, and patent applications cited herein are incorporated by reference in their entireties for all purposes.

VI. EXAMPLES

Example 1

Monoclonal Antibodies

Monoclonal Antibodies to the Beta-β Subunit of Inhibin/Activin

A. Immunization

Mice were immunized in a similar procedure to that described by Wong et al. (1993) *J. Immunol. Methods* 165: 1, using recombinant mature *Xenopus laevis* activin B, to produce monoclonal antibodies from lymph node fusions. The immunization protocol also incorporated the repetitive immunizations, multiple sites (RIMMS) technique. Immunizations were given subcutaneously in proximity to draining lymph nodes (Caterson et al. (1983) *J Biol. Chem.* 258:8848, Wring et al. (999) *J. Pharm. Biomed. Anal.* 19:695). Initial immunizations were performed using Freund's complete adjuvant, with subsequent boosts using RIBI adjuvant. *X. laevis* and human mature inhibin/activin βB subunit share 96.5% identity (Pearson et al. (1997) *Genomics* 46:24) with only four amino acids different. The *X. laevis* activin B was expressed in E. coli as inclusion bodies, refolded to native, dimeric form and purified by a combination of reverse phase and ion exchange chromatography (Department of Biochemistry, University of Cambridge).

B. Development of Monoclonal Antibodies

Sp2/0 myeloma cells were fused to the B-lymphocytes obtained from the lymph nodes using PEG (Harlow and Lane *Immunoaffinity purification* In: Antibodies: A Laboratory Manual 1988). Cloning and recloning of the initial antibody secreting cell lines were performed in ClonaCell® methylcellulose (StemCell Technologies SARL, London, UK, cat: 03804) with individual colonies being picked. Antibody purification was achieved by Protein G (Millipore, Billerica, Mass., US) affinity chromatography (Harlow and Lane, 1988). The ability of the antibodies to recognize the βB subunit was assessed by screening them using a solid-phase antibody capture ELISA against *X. laevis* activin B (as used for immunization) and human activins A and B, inhibin B (R&D Systems Europe Ltd, Abingdon, Oxfordshire, UK).

Following the lymph node fusion, 2000 growing clones were picked from methylcellulose and screened (using a solid-phase antibody capture ELISA format) against *X. laevis* activin B, human activin B, human inhibin B and human activin A. The high extent of sequence conservation between human beta-A and -B subunits presents a considerable challenge to discovery of an antibody specific for a single beta subunit. Only three antibodies of 2000 were highly specific to the human βB subunit (rather than βA) and recognized this subunit both in human activin B and inhibin B. From the original 2000 clones picked, another four clones were totally specific for *X. laevis* activin B, recognizing neither human activin nor inhibin. Some antibodies recognized *X. laevis* activin B, human activin and inhibin B, and human activin A equally. Clone 46 ($IgG_1$) gave the highest absorbance when screened against the *X. laevis* and human activin B, and did not recognize human activin A. Clone 46 was recloned twice to give 46A/F. Further immunoassay work concentrated on antibody 46A/F.

C. Sequencing of Monoclonal Antibody 46A/F

Sequencing of the variable regions of 46A/F was performed by Fusion Antibodies Ltd, Sprirngbank Industrial Estate, Pembroke Loop Road, Belfast, N. Ireland. Total RNA was extracted from the hybridoma cell pellets using Fusion Antibodies Ltd in-house RNA extraction protocol.

D. RT-PCR cDNA was created from the RNA by reverse-transcription with an oligo(dT) primer. PCR reactions using variable domain primers to amplify both the VH and VL region of the monoclonal antibody DNA. The amplification products were separated by gel electrophoresis and purified. VH and VL PCR products were cloned into the Invitrogen sequencing vector pCR2.1 and transformed into TOP10 for positive transformants. Selected colonies were picked and analyzed through sequencing.

The amino acid sequences of the variable regions of the 46A/F antibody described herein include:

SEQ ID NO. 1: Monoclonal antibody 46A/F VL region 1-170.
MDFQVQIFSFLLISASVIMSRGQIVLTQSPAIMSASLGERVTMTCTASSS

VSSSYFHWYQQKPGSSPKLWIYSTSNLASGVPARFSGSGSGTSYSLTIST

MEAEDAVTYYCHQYHRSPWTFGGGTKLEIKRADAAPTVSIFPPSSEQLTS

GGASVVCFLNNFYPK

-continued
SEQ ID NO. 2: Monoclonal antibody 46A/F VH region 1-174.
MKCSWIMFFLVATATGVHSQVQLQQPGAELVKPGASVKLSCKASGYTFT

NYWMYWVKQRPGQGLEWIGMIHPNSGSTNYNGKFKTGATLTVDKSSSTV

YMQLSSLTSEDSAVYYCARWGYGGNYDYAMDYWGQGTSVTVSSAKTTPP

SVYPLAPGSL

Monoclonal Antibody to the Alpha-Subunit of Inhibin

A. Fragmentation of R1

Monoclonal antibody R1 ($IgG_{2a}$), raised to the alpha subunit of inhibin (Groome et al. (1990) *Hybridoma* 9:31), was digested into F(ab')$_2$ fragments by using lysyl endopeptidase (Wako Chemicals GmbH, Neuss, Germany, cat: 125-02543) as described by Yamaguchi et al. (1995) *J. Immunol. Methods* 181:259. Any intact R1 and Fc fragments were removed by purification with Protein A (Millipore, Billerica, Mass., US), and whole R1 to F(ab')$_2$ reduction was monitored by SDS-PAGE. The F(ab')$_2$ fragments were treated with 2-mercaptoethylamine HCl (MEA, Pierce, Ill., US, cat: 20408) to yield Fab' fragments. The protocol used to reduce the F(ab')$_2$ Fragments to Fab' with MEA was as per instructions in the MEA package insert, with the reaction buffer containing 1 mM $MgCl_2$, 0.1 mM $ZnCl_2$ and 5 mM EDTA. Reduction of F(ab')$_2$ to Fab' was assessed by HPLC using a Superdex 200 column (Sigma-Aldrich, Dorset, UK).

The proteolytic digestion of monoclonal antibody R1 to F(ab')$_2$ fragments by lysyl endopeptidase was successful. After this, the reduction to the Fab' fragment and biotinylation were carried out as described.

F. Biotinylation of R1

The R1 Fab' fragments were biotinylated with EZ-link Sulfo-NHS-LC-Biotin (Biotin, Pierce, Ill., US, cat: 21335). R1 Fab' fragments were dialysed in 0.1 M $NaHCO_3$, and then were diluted in 0.1 M $NaHCO_3$ to give a concentration of 1 mg/ml. The concentration of R1 Fab' was determined by reading the absorbance at 280 nm. The biotin was made up immediately prior to use by adding 2 mg to 1 ml of pure water in a glass vial. 100 µL of the 2 mg/ml biotin was added per mg of R1 Fab', which was then incubated at room temperature for 3 h whilst gently mixing. The reaction was stopped by adding 100 µL of 1 M $NH_4Cl$ per ml of R1 Fab', then was incubated for 10 min at room temperature. The biotinylated R1 Fab' was dialysed in PBS for 2 days at 2-8° C. to remove any excess biotin. 0.1% sodium azide was added as a preservative for storage at 2-8° C.

Example 2

Improved Inhibin B Assay

A. Coating of Microtiter Plates

Maxisorp microtiter plates obtained from Nune (Roskilde, Denmark, cat: 439454), were coated with 100 µL/well of 10 µg/ml 46A/F in bicarbonate buffer (BupH Carbonate-Bicarbonate Buffer Pack, PIERCE, Rockford, Ill., US, cat: 28382), overnight at 4° C. The excess antibody was removed, then the plates were washed once in PBS (Sigma-Aldrich, Dorset, UK, cat: P4417-100TAB). The plates were blocked with 150 µL/well of 0.5× casein buffer (diluted from 5× stock in PBS (same as PBS in assay protocol), Mast Group Ltd, Bootle, Merseyside, UK, cat: CLB-M2052) and 6% (w/v) sucrose (VWR International Ltd, Lutterworth, Leicestershire, UK, cat: 102747E) for 2 h at room temperature. The contents of the plates were removed, before the plates were dried in a dehumidifying chamber overnight, and foil packed with desiccant for storage at 2-8° C.

B. Standard Curve

Inhibin B standards were made in foetal calf serum (FCS, Invitrogen, Paisley, UK, cat: 10108-157) using recombinant inhibin B from R&D Systems Europe Ltd (Abingdon, Oxfordshire, UK, cat: 677-IB/CF). The standards were calibrated with the WHO inhibin B reference reagent (NIBSC, Potters Bar, UK, cat: 96/784), which was diluted in FCS to create a standard curve in which to calibrate the recombinant standards.

C. Assay Procedure (Two-Site ELISA)

50 μL of 1× high performance Enzyme-Linked Immunosorbent Assay (ELISA) buffer (HPE, diluted from 5× stock in water, Mast Group Ltd, Bootle, Merseyside, UK, cat: CLB-M1940) including 10 mg/ml (w/v) bovine γ-globulins (Sigma-Aldrich, Dorset, UK, cat: G7516-25G) was added to each well. 50 μL/well of standards and samples were added, and then the plate was incubated overnight at room temperature. The contents of the plate were removed, and then the plate was washed 4 times with PBS (Sigma-Aldrich, Dorset, UK, cat: P4417, 0.01 M phosphate buffer, 0.0027M potassium chloride and 0.137M sodium chloride, pH 7.4) and 0.05% Tween 20 (wash buffer) (Sigma-Aldrich, Dorset, UK, cat: P1379-500 mL). 100 μL/well of freshly diluted biotinylated R1 Fab' (at 0.125 μg/ml) in 1× casein (diluted from 5× stock in PBS, Mast Group Ltd, Bootle, Merseyside, UK, cat: CLB-M2052) with 2.5% (v/v) heterophilic blocking reagent (HBR, Scantibodies Laboratory Inc, Santee, Calif., cat: 3KC533) was added for 1 h at room temperature. The contents of the plate were removed, and then the plate was washed 4 times with wash buffer. 100 μL/well of freshly diluted streptavidin poly HRP (Mast Group Ltd, Bootle, Merseyside, UK, cat: CLB-M2051) at 0.4 μg/ml in casein (1×) was added for 1 h at room temperature. The contents of the plate were removed, the plate was washed 4 times with wash buffer, the plate was washed a further 3 times with distilled water. TMB peroxidase substrate and Peroxidase substrate solution B (Insight Biotechnology Ltd, Wembley, UK, cat: 50-76-00) were mixed 1:1 prior to use, and 100 μL/well was added for 25 min at room temperature. 100 μL of 6% phosphoric acid (VWR International Ltd, Lutterworth, Leicestershire, UK, cat: 294206Q) was added to each well to stop the reaction. The absorbance values of each well were measured using an automated microplate reader (Benchmark microplate reader, Bio-Rad Laboratories, Hercules, Calif., US) and compatible software Microplate Manager 5.2 (Bio-Rad Laboratories, Hercules, Calif., US), using a measurement λ of 450 nm and a reference λ of 655 nm. The initial part of the standard curve was linear with a 5PL Cook or Rodbard fit usually fitted if it curved near the top.

D. Validation of the Improved Inhibin B Assay

The validation of the improved assay was determined using an overnight sample incubation.

Previously collected human serum samples from 29 donors (15 female and 14 male) was tested for inhibin B concentration on both the DSL assay (Diagnostic Systems Laboratories, Webster, Tex., US) and the present improved assay. The DSL inhibin B ELISA was carried out in line with the instructions in the package insert. The serum had been separated within 4 h of collection, and was then stored at −40° C. until used in the assays. Ethical approval was obtained from the Barking and Havering Health authority and all patients gave informed consent to participate in the study to measure inhibin B.

Post-menopausal serum (PMS) samples (n=30) (Innovative Research, Inc, Southfield, Mich., cat: IPLA-SER) from women over 56 years of age were used to establish whether the new inhibin B assay would give the low inhibin B results associated with the post-menopausal state. The samples had been previously tested in an anti-Müllerian hormone (AMH) assay where all samples had levels of AMH below the detection limit (<50 pg/ml) of the assay. PMS samples are particularly useful in studies looking at false positives in inhibin B assays, as the levels of serum from post-menopausal women should be minimal or zero. The PMS samples were also tested on the DSL inhibin B assay (n=29) with the serum samples described above.

E. Sensitivity

The detection limit of the assay was determined by the mean absorbance of the blank replicates (n=10)+3 standard deviations ($B_0+3SD$) (O'Fegan, 2000).

The detection limit of the assay was 4.6 pg/ml. The range of calibrated recombinant human inhibin B standards used in the improved assay was 1046.5 to 4 pg/ml (FIG. 1). Subsequent work established that similar sensitivity could be observed with minor adjustments to the secondary antibody and streptavidin poly HRP concentrations using sample incubation periods of 1 to 2 h.

F. Specificity

All three structurally related proteins, inhibin A, activin A and activin B, were assayed in the improved inhibin B assay at excess concentrations, 100 ng to 1 mg/ml. The 46A/F antibody demonstrated 0.004%, 0.0006% and 0.005% cross-reactivity, respectively. The cross-reactivity of inhibin A (Genentech) in the OBI inhibin B ELISA was 0.03% and in the DSL inhibin B ELISA 0.004%. The absorbance of the tested analyte is read from the standard curve to give an estimated concentration value. Cross reactivity was calculated as follows:

$$\text{Actual concentration used/Estimated concentration} = \text{Division factor}$$

$$100/\text{Division factor} = \% \text{ Cross reactivity}$$

G. Recovery

The mean percentage recovery from spiked human serum samples was 86.92±8.03.

Recovery was determined by spiking various human serum samples (n=28) with a single dose of a known amount of recombinant human inhibin B (100 pg/ml).

$$\text{Recovery (\%)} = \frac{\text{measured amount} - \text{endogenous amount}}{\text{added amount}} \times 100$$

H. Accuracy of Dilutions

All of the samples had slopes that were not significantly different from zero, which showed that the samples gave linear results when diluted. The percentage values can be seen in Table 1.

Six samples were diluted over a range in FCS and assayed, to assess whether serum samples give accurate results when diluted. Expected values were calculated by dividing the concentration from the undiluted sample by the dilution factor used. Percentage recovery was calculated by dividing the observed values by the expected values and multiplying by 100. The mean values (pg/ml) were multiplied by their relevant dilution factor. A trendline was fitted to each sample's data at each dilution, and linear regression was performed to determine whether the slope was significantly different from zero. Samples with a slope which was not significantly different from zero were accepted as having linear results when diluted.

TABLE 1

Expected and observed values of diluted serum samples in the improved inhibin B assay.

|  |  | Observed (pg/ml) | Expected (pg/ml) | % Recovery |
|---|---|---|---|---|
| Sample 1 | Undiluted | 573.813 | 573.813 | 100.000 |
|  | 1 in 2 | 291.982 | 286.907 | 101.769 |
|  | 1 in 4 | 135.852 | 143.453 | 94.701 |
|  | 1 in 8 | 60.142 | 71.727 | 119.262 |
| Sample 2 | Undiluted | 528.995 | 528.995 | 100.000 |
|  | 1 in 2 | 253.457 | 264.498 | 95.826 |
|  | 1 in 4 | 140.625 | 132.249 | 106.334 |
|  | 1 in 8 | 76.578 | 66.124 | 115.809 |
| Sample 3 | Undiluted | 120.185 | 120.185 | 100.000 |
|  | 1 in 2 | 60.498 | 60.093 | 100.675 |
|  | 1 in 4 | 32.699 | 30.046 | 108.829 |
|  | 1 in 8 | 16.619 | 15.023 | 110.623 |
| Sample 4 | Undiluted | 364.381 | 364.381 | 100.000 |
|  | 1 in 2 | 156.978 | 182.191 | 86.161 |
|  | 1 in 4 | 81.757 | 91.095 | 89.749 |
|  | 1 in 8 | 42.238 | 45.548 | 92.734 |
| Sample 5 | Undiluted | 301.969 | 301.969 | 100.000 |
|  | 1 in 2 | 149.892 | 150.985 | 99.276 |
|  | 1 in 4 | 78.759 | 75.492 | 104.327 |
|  | 1 in 8 | 40.330 | 37.746 | 106.845 |
| Sample 6 | Undiluted | 259.453 | 259.453 | 100.000 |
|  | 1 in 2 | 158.613 | 129.727 | 122.267 |
|  | 1 in 4 | 77.123 | 64.863 | 118.901 |
|  | 1 in 8 | 37.333 | 32.432 | 115.113 |

I. Inter- and Intra-Assay Variability or Precision

Both inter- and intra-assay variability, % CV, were less than 8%. Precision was expressed as percent coefficient of variation (% CV) for both inter- (n=6) and intra-assay (n 32) variability (O'Fegan, 2000).

J. Statistical Analysis

Linear regression was performed on data obtained from comparing human serum samples on both the improved inhibin B assay and the commercially available DSL inhibin B assay using GraphPad Prism version 4.00 for Windows (GraphPad Software, San Diego, Calif., USA).

Example 3

Physiological Investigations

A. Post Menopausal Samples and Heterophilic Antibody Interference

Post-menopausal serum (PMS) from 30 women was used to check that the new inhibin B assay would give expected inhibin B measurements with no false positives. The 30 samples were assayed and all samples but one were measured at <10 pg/ml. One sample however had a measurement of ~100 pg/ml. This result was further investigated and found to be a false positive result arising from heterophilic antibody interference. The addition of 2.5% (v/v) HBR at the detection antibody addition stage brought the apparent inhibin B measurement down to 13 pg/ml. The addition of the HBR to the assay did not affect the measurements of inhibin B of the other samples tested or affect the recovery of inhibin B when spiked into these PMS samples.

B. Serum Samples Tested with DSL and Improved Inhibin B Assays

Inhibin B measurements from both the DSL and improved assays gave a significant positive linear correlation (r=0.98; P<0.0001; FIG. 2). The improved assay however, measured slightly higher inhibin B concentrations (average of 2 times that of the DSL assay).

The improved inhibin B assay using 46A/F as the capture antibody, simplifies the assay and improves the sensitivity and specificity. Antibody 46A/F does not need oxidation of the βB subunit to bind, nor does it need the accompanying SDS and heat treatment. All of these simplify the performance of the assay and its reliability.

The cell fusion to produce the hybridomas was carried out using lymph nodes rather than the more routinely used spleen fusion method. Lymph nodes were chosen due to previous successful fusions to produce monoclonal antibodies to weak antigens (Mirza et al. (1987) *J. Immunol. Methods* 105:235; Kishiro et al. (1995) *Cell Struct. Funct.* 20:151; Sado et al. (2006) *Acta Histochem. Cytochem.* 39:89). The use of a lymph node fusion, using RIMMS, also allowed immunization with very small amounts of antigen. Mirza et al. (1987) reported the production of greater numbers of antibody-secreting hybridomas with fusions from lymph node lymphocytes immunized locally than with fusions from subcutaneous immunizations resulting in a splenic lymphocyte fusion. Our experience showed that although a small number of candidate antibodies emerged from our fusion, some of these were of exceptional quality.

Although 2000 growing clones were picked from the lymph node fusion, only five recognized human inhibin B. Out of these five antibody secreting clones, two of these (8 and 55) recognised *X. laevis* activin B and both human activins A and B, and human inhibins A and B, which made them unsuitable for a specific inhibin B assay. Three of the five clones (24, 35 and 46) produced antibodies that recognized only *X. laevis* activin B, human activin B and human inhibin B, which made all of these potential capture antibodies in an inhibin B assay. A further four antibody secreting clones only recognised *X. laevis* activin B. *X. laevis* activin B and human activin B differ by only 4 amino acids. These results gave an indication to how difficult it was to produce good antibodies to the βB subunit of inhibin B for use in ELISAs. During the immunization procedure murine self-tolerance was not broken, since it was shown by immunohistochemistry that neither antibodies 24, 35 or 46A/F recognized mouse tissue. The three antibodies (24, 35 and 46A/F) that recognised *X. laevis* and human activin B and human inhibin B were used to stain ovary sections from human, sheep, rat and mouse species. Only human samples gave positive immunohistochemistry results. The OBI and DSL assays can be used to detect inhibin B in mouse and rat species (Woodruff et al. (1996) *Endocrinology* 137:5463).

As mentioned earlier the reaction of the previous capture monoclonal antibody (C5) with its epitope is critically dependant on the oxidation state of the methionines in the sequence MSM in the βB subunit. The oxidation creates a new epitope to which self-tolerance does not exist. This was probably the reason why the C5 antibody recognized both mouse and human βB subunit.

In contrast, the 46A/F antibody recognizes the human βB subunit independently of an oxidation state. From the view of immunoassay the need for sample oxidation creates unnecessary complexity. For example, the oxidation state of different recombinant inhibin B standards (e.g. DSL or R&D Systems) is unknown and possibly variable. Furthermore, the extent of oxidation of inhibin B in serum samples and standards may differ in different assay formats.

The standards used in the new inhibin B assay were calibrated against the WHO inhibin B reference reagent from NIBSC. This standard is comprised of a mixture of inhibin forms immunopurified from human follicular fluid. The calibration of the recombinant inhibin B standards allowed the measurements to be reliable and standardized. The present assay uses commercially available assay diluents and detection reagents making it easy to reproduce. The assay uses antibody 46A/F which is extremely specific, and no sample pre-treatment is required. The lack of oxidation, detergent, and heat treatment allow a wider range of samples to be used, The use of the R1 Fab' fragment for detection of the α subunit is to reduce non-specific binding that may occur, due to the lack of the Fe region (Lamoyi (1986) *Methods Enzymol.* 121:652; Milenic et al. (1989) *J. Immunol. Methods* 120:71; Fowers et al. (2001) *J. Drug Target* 9:281). The use of passive and active blockers of heterophilic antibody interference (HBR and bovine γ-globulins) in immunoassays, helps to eliminate false positives. All of these characteristics offer the prospect of greater robustness.

The sensitivity of the new assay (4.6 pg/ml) was not greatly different from the previous DSL assay (7 pg/ml), but can be achieved without the overnight incubation used in both the OBI and DSL inhibin B ELISAs. The cross-reactivity of inhibin A, activin A and activin B in the improved assay was 0.004%, 0.0006% and 0.005% respectively.

Good recovery in human serum was observed (86.92%±8.03), with samples showing linearity when diluted. The inter- and intra-assay variability of the new assay was <8%. While the present example describes overnight incubation, acceptable standard curves can be generated in as short a period as 1 h. The performance characteristics of the new inhibin B assay are now comparable to the inhibin A assays, which have proved suitable for short incubation period assays on both microplate (DSL) and random access immunoassay analysers (Beckman).

Detection of potential false positives in the inhibin B assay PMS is of great value. As described herein, a false positive result from heterophilic antibody interference in a PMS sample can be corrected by the addition of a blocking reagent. Human anti-species antibodies have been reported to be found in anything from 1 to 80% of a population (Kricka (1999) *Clin. Chem.* 45:942; Andersen et al. (2004) *J. Immunoassay Immunochem.* 25:17). These antibodies can cause interference in immunoassays and result in a false positive (Weber et al. (1990) *Scand. J. Clin. Lab Invest.* Supp. 201:77; Morgan and Tarter (2001) *J. Urol.* 166:2311; Ismail et al. (2002) *Clin. Chem.* 48:2023; Marks (2002) *Clin. Chem.* 48:2008). False positive results in inhibin A assays have recently been reported during pre-natal screening for Down's syndrome (Lambert-Messerlian et al. (2007) *Clin. Chem.* 53:800). False positives due to heterophilic antibody interference in the improved inhibin B assay were addressed by using 2.5% HBR and 10 mg/ml bovine γ-globulins in the final protocol. The HBR is an active blocker of human anti-murine antibodies, whereas the bovine γ-globulins are passive blockers for human anti-bovine antibodies. Studies have tested samples with and without HBR to identify false positive results (Morgan and Tarter, 2001; Marks 2002). While the HBR used in the present study did not entirely correct the result considered to be a false positive, the correction is certainly an improvement and likely to be sufficient for most purposes.

The improved inhibin B assay correlated positively to the current DSL assay (r=0.98). The improved inhibin B assay however, gave results on average that were apparently two times greater than those obtained with the DSL assay. A number of factors account for this apparent difference. Due to the production processes used to obtain recombinant material to use as standards in the assays, there may be subtle changes in the way the capture antibody recognizes inhibin B in samples compared to how it recognizes recombinant forms. For example, the recombinant inhibin B used in the standards can be oxidized during the preparation process (Knight and Muttukrishna, 1994), which would enable the DSL capture antibody to recognize the oxidized recombinant material immediately, but longer to recognize inhibin B in serum. The improved inhibin B assay can also measure more of the inhibin B available in a sample, as the oxidation step uses a certain amount of $H_2O_2$ added to the sample. Although the amounts of inhibin B can vary considerably between samples, it is difficult to know the proportion of inhibin B that has been oxidised. The proportion of inhibin B that can be oxidised is compromised by serum samples that are haemolysed. The lack of the oxidation step in the present improved assay thus removes yet another source of variation from the immunoassay.

Example 4

Use of Inhibin B ELISA for Human, Monkey and Rat

We applied the improved two-step sandwich-type enzymatic microplate assay described above to measure Inhibin B levels within 3.5 hours. The assay measures Inhibin B in 50 μL of serum sample against Inhibin B calibrators (10-1000 pg/1 mL). As explained above, the inhibin B assay does not cross-react with Inhibin A, Activin A, Activin B, Activin AB, AMH, FSH, LH or Follistatin 315 at 2 times physiological concentrations.

We used the Inhibin B Gen II assay to measure inhibin B in human, rat and monkey specimens. For human specimens, total imprecision was 4.6% at 19.1 pg/mL, 4.5% at 75.8 pg/mL, and 4.9% at 272.6 pg/mL. The functional sensitivities at 10% and 15% CV were 9.3 pg/mL and 5.6 pg/mL, respectively. Dilution and spiking studies showed average recoveries of 90-110%. For adult male Sprague Dawley rat specimens total imprecision was 8.6% at 159.9 pg/mL for plasma and 7.3% at 96.2 pg/in L for serum (see Table 2). For adult female Sprague Dawley rat serum specimens total imprecision was 3% at 156.8 pg/mL. For adult male Wistar Hanover rats total imprecision was 5.6% at 165.4 pg/mL for plasma and 7.3% at 139.2 pg/mL for serum (see Table 3). Dilution studies showed average recoveries of 85 to 115% for rat specimens. Male Rhesus Monkey sera also showed measurable levels of inhibin B ranging from 500 to 1500 pg/mL.

TABLE 2

Inhibin B levels in specimens from adult male Sprague Dawley rats

|  | Mean (pg/mL) | % CV |
|---|---|---|
| Rat 1 (plasma) | 159.7 | 8.06 |
| Rat 2 (plama) | 169.9 | 6.9 |
| Rat 3 (serum) | 96.3 | 7.3 |
| Rat 4 (serum) | 223.1 | 8.7 |

TABLE 3

Inhibin B levels in specimens from adult male Wistar Hanover rats

|  | Mean (pg/mL) | % CV |
|---|---|---|
| Rat 1 (plasma) | 165.5 | 5.1 |
| Rat 2 (plama) | 182.1 | 5.6 |
| Rat 3 (serum) | 139.2 | 7.2 |
| Rat 4 (serum) | 149.3 | 6.1 |

What is claimed is:

1. An isolated monoclonal antibody specific for an inhibin/activin beta-B subunit polypeptide, the antibody comprising a heavy chain variable region comprising three heavy chain complementarity determining region (CDR) from the heavy chain variable region sequence of SEQ ID NO:2 and a light chain variable region comprising three light chain CDR from the light chain variable region sequence of SEQ ID NO:1, wherein binding of said antibody does not require oxidation of said inhibin beta-B subunit polypeptide or antibody-binding epitope thereof.

2. The monoclonal antibody of claim 1, wherein said antibody comprises a light chain variable region sequence of SEQ ID NO:1.

3. The monoclonal antibody of claim 1, wherein said antibody comprises a heavy chain variable region sequence of SEQ ID NO:2.

4. The monoclonal antibody of claim 1, wherein said antibody cross-reacts with the inhibin/activin beta-A subunit polypeptide less than 0.01%.

5. The monoclonal antibody of claim 1, wherein the antibody is conjugated to a detectable moiety.

6. The monoclonal antibody of claim 5, wherein the detectable moiety is a selected from the group consisting of fluorophores, luminescent labels, metal complexes, radioactive labels, and enzymes.

7. The monoclonal antibody of claim 1, wherein the antibody is conjugated to a solid support.

8. The monoclonal antibody of claim 1, wherein the antibody is conjugated to biotin or streptavidin.

* * * * *

UNITED STATES PATENT AND TRADEMARK OFFICE
CERTIFICATE OF CORRECTION

PATENT NO. : 8,383,351 B2
APPLICATION NO. : 12/482961
DATED : February 26, 2013
INVENTOR(S) : Groome et al.

It is certified that error appears in the above-identified patent and that said Letters Patent is hereby corrected as shown below:

In the Specification

Col. 19, line 35: "(n 32)" should read --(n = 40)--

Col. 19, line 40: "DSL inbibin" should read --DSL inhibin--

Col. 20, line 4: "the PB subunit" should read --the βB subunit--

Col. 20, line 47: "the methionincs in the" should read --the methionines in the--

Col. 22, line 38: "96.2 pg/in L for" should read --96.2 pg/mL for--

Signed and Sealed this
Eighteenth Day of February, 2014

Michelle K. Lee
*Deputy Director of the United States Patent and Trademark Office*